United States Patent
Short et al.

(10) Patent No.: US 6,916,315 B2
(45) Date of Patent: Jul. 12, 2005

(54) METHODS OF OPERATING A PHOTO-THERMAL EPILATION APPARATUS

(76) Inventors: Kenneth Lawrence Short, 142 Quaker Path, Setauket, NY (US) 11733; Howard Stephen Bertan, 41 Moss La., Jericho, NY (US) 11753

( * ) Notice: Subject to any disclaimer, the term of this patent is extended or adjusted under 35 U.S.C. 154(b) by 204 days.

(21) Appl. No.: 10/265,965

(22) Filed: Oct. 7, 2002

(65) Prior Publication Data

US 2004/0068255 A1 Apr. 8, 2004

(51) Int. Cl.⁷ .............................................. A61B 18/18
(52) U.S. Cl. ............................... 606/9; 606/10; 606/12; D14/383; D14/388; 705/72
(58) Field of Search .................. 606/9–12; 705/72–77; D14/383–419

(56) References Cited

U.S. PATENT DOCUMENTS

| | | | |
|---|---|---|---|
| 3,693,623 A | 9/1972 | Harte et al. | 128/303.1 |
| 3,834,391 A | 9/1974 | Block | 128/303.1 |
| 4,388,924 A | 6/1983 | Weissman et al. | 128/303.1 |
| 4,617,926 A | 10/1986 | Sutton | 128/303.1 |
| 4,743,809 A | 5/1988 | Vlahos | 315/209 |
| 5,026,369 A | 6/1991 | Cole | 606/36 |
| 5,105,126 A | 4/1992 | Girard, Jr. | 315/241 |
| 5,226,907 A | 7/1993 | Tankovich | 606/133 |
| 5,381,077 A | 1/1995 | McGuire | 315/247 |
| 5,425,728 A | 6/1995 | Tankovich | 606/9 |
| 5,595,568 A | 1/1997 | Anderson et al. | 606/9 |
| 5,735,844 A | 4/1998 | Anderson et al. | 606/9 |
| 5,860,967 A * | 1/1999 | Zavislan et al. | 606/9 |
| 6,050,990 A * | 4/2000 | Tankovich et al. | 606/9 |
| 6,110,195 A * | 8/2000 | Xie et al. | 607/89 |
| 6,149,644 A * | 11/2000 | Xie | 606/9 |
| 6,267,780 B1 * | 7/2001 | Streeter | 607/89 |
| 6,447,503 B1 * | 9/2002 | Wynne et al. | 606/9 |
| 6,461,348 B1 * | 10/2002 | Bertan et al. | 606/9 |
| 6,508,813 B1 * | 1/2003 | Altshuler | 606/9 |
| 6,533,776 B2 * | 3/2003 | Asah et al. | 606/9 |
| 6,723,090 B2 * | 4/2004 | Altshuler et al. | 606/9 |

* cited by examiner

Primary Examiner—A. Farah
(74) Attorney, Agent, or Firm—Island Patent; F. Scott Tierno

(57) ABSTRACT

Methods of operating and logging the usage of a photo-thermal epilation apparatus provide for the logging of usage information as the apparatus is employed for each epilation session. The operational information may be applied to determine when calibration is required, if additional usage funds must be paid before additional sessions may be conducted, and or when and who conducted epilation sessions with the apparatus. A usage log may be stored within a database that contains entries of operation or usage information. Each usage log entry may include information associated with a client, an operator, as well as other useful information related to the usage of the apparatus. The apparatus may further be configured to communicate with at least one remote computer. The communication with the remote computer may be included for enabling operation and usage of the apparatus to be metered, monitored, and or purchased in pre-determined usage allotments.

14 Claims, 11 Drawing Sheets

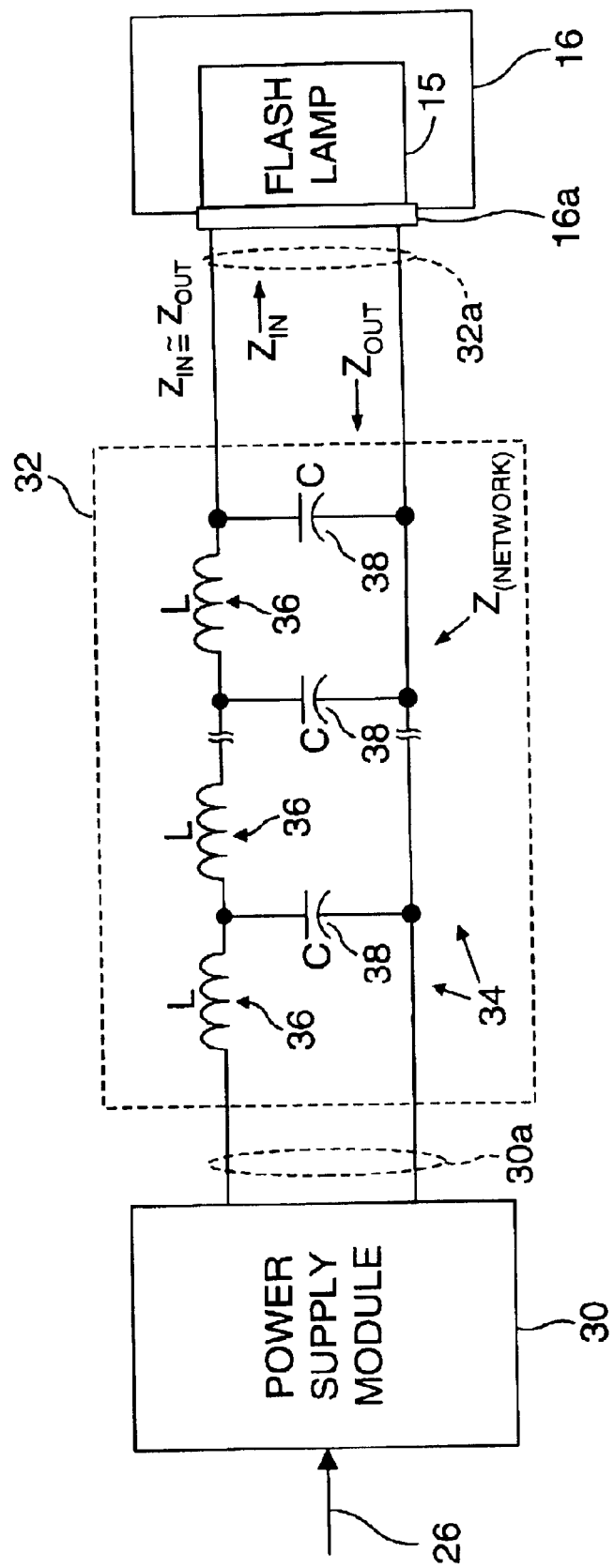

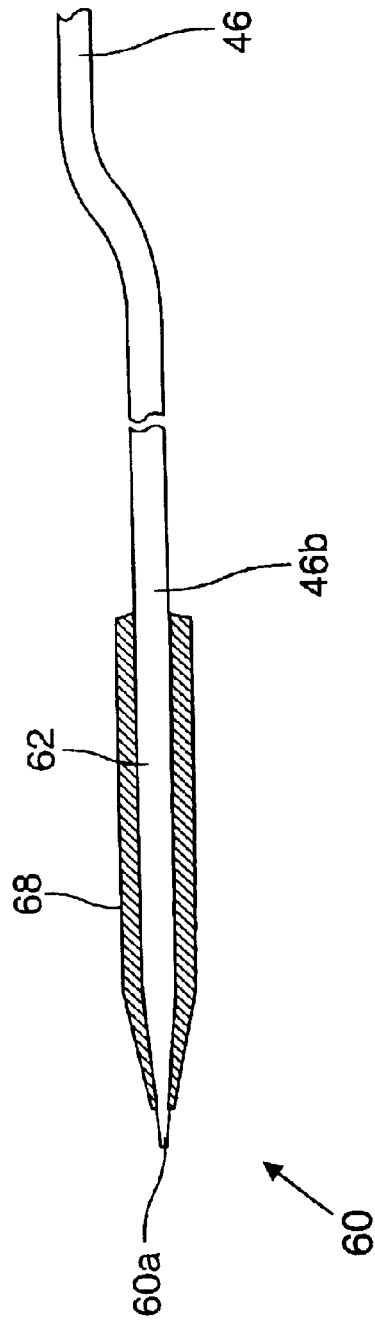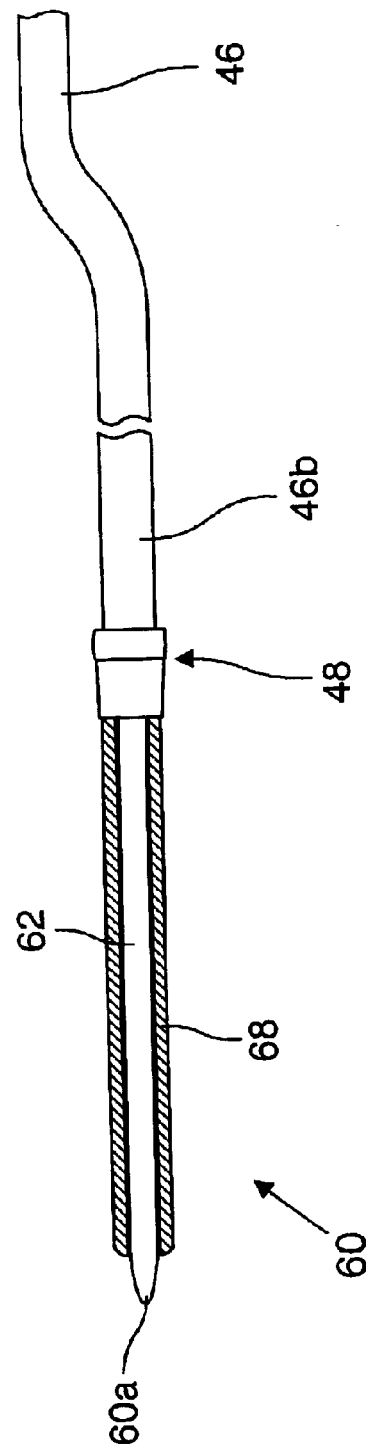

METHODS OF OPERATING A PHOTO-THERMAL EPILATION APPARATUS

CROSS REFERENCE TO RELATED APPLICATIONS

The subject matter provided herein is related to copending application Ser. No. 09/384,122 filed on Aug. 27, 1999, now U.S. Pat. No. 6,461,348, which is hereby incorporated by reference.

TECHNICAL FIELD

The present invention relates generally to systems that effect permanent hair removal. More particularly, the invention relates to methods of operating, and monitoring and recording the usage of photo-thermal epilation apparatus.

BACKGROUND DESCRIPTION AND PRIOR ART

Permanent hair removal can be realized by several known techniques, including electrolysis and photo-thermal epilation. Each of these methods involves the destruction of a nutrient providing area at the base of the follicle. This area or region is known as the papilla, which may also be termed 'growth support tissue' of the follicle. The growth support tissue is supplied with nutrients by capillary blood vessels. It is well known in the art that simply (physically) removing a hair will not prevent another from growing in its place. To achieve permanent hair removal the growth support tissue at the base of the follicle must be destroyed.

Apparatus to which the present invention apply are structured to deliver high energy light pulses to the base of the follicle. Accordingly, these apparatus employ high energy light pulses to photo-coagulate the growth support tissue of a succession of follicles by delivering pulsed light energy of a sufficient energy level, having a sufficiently short duration, resulting in the destruction of the growth support tissue of selected follicles.

When considering the operation and maintenance of a photo-thermal epilation apparatus, a number of problems and concerns arise. These problems may be exacerbated by the fact that the apparatus are often utilized in salons and offices wherein relatively unskilled and minimally trained individuals operate the apparatus. For example, one area of concern is associated with the reliable and safe operation of these apparatus. In particular, it would be helpful to provide periodic and automatic reminders when calibration and maintenance is required. As skilled persons will appreciate, light producing elements of photo-thermal epilation apparatus, such as xenon flash lamps, experience a drop off of light output as the flash lamp ages. This results in a loss of energy being delivered to the follicle and improper or incomplete photo-coagulation. Accordingly, it is necessary to periodically calibrate photo-thermal epilation instruments so that the desired light intensity (and energy level) produced and delivered to selected follicles is maintained within a desired range or at a desired level. The present prior art epilation devices are lacking in their ability to quickly verify proper calibration, and if necessary, block operation when servicing is required.

Another concern that arises with the usage of epilation apparatus is associated with the monitoring of each usage, and ensuring that payments made for that usage are accounted for. It would be most desirable to generate a record, which may be readily reviewed by authorized individuals such as managers and owners, that clearly shows each usage, and thereby provides a mechanism for verifying that all revenue that should have been collected for the operation of the apparatus, has been collected and is accounted for. The above discussed monitoring and payment collection issues are somewhat exacerbated when services are rendered to customers or clients that pay with cash. Therefore, when considering businesses that commonly provide epilation services, it is difficult for an owner who spends a limited number of hours at the business location to verify that all collected receipts have actually been accounted for. When considering the use of a typical epilation apparatus, which does not include a data logging capability, employees may simply not record an appointment (if appointments are recorded at all), and subsequently pocket a cash payment resulting from the 'undocumented' session.

Therefore, when considering the above discussed problems, and others known to skilled persons, there is a need to provide new and improved photo-thermal epilation apparatus, and methods of operating and monitoring the usage thereof. A number of characteristics, principles, and associated novel features of the present invention, will become clear from the description and figures provided herein. Attention is called to the fact, however, that the drawings are illustrative only. In particular, the embodiments included and described herein, have been chosen in order to best explain a number of operating principles of the invention, and their practical application, to thereby enable skilled persons to best utilize the invention and a wide variety of embodiments. Accordingly, all variations possible are contemplated as being part of the invention, limited only by the scope of the appended claims.

SUMMARY OF THE INVENTION

In accordance with the invention, methods of operating photo-thermal epilation apparatus are provided. The methods provide for a monitoring and recording of information associated with each of a plurality of sessions conducted with the apparatus. It may be noted that most preferred apparatus of the invention will include electronic circuitry, possibly including a local or embedded computer, that supports the various steps of the methods of the invention. It may further be noted that the methods of the invention can be employed for data logging, including building and maintaining an up-to-date database of client information. Such data logging and information collecting may be termed record keeping. Exemplary record keeping activities will preferably include automatic billing and or automatic accounting functions.

Preferred methods of the invention may commence with an identifying and authorizing of an operator attempting to conduct an epilation session. Such an identifying, if included, may be realized by a number of available means. For example, one simple identifying means may involve the use of a plurality of pushbuttons, say provided as a portion of a keypad of a user interface, wherein an operator enters an assigned operator code. Alternately, the operator may use a magnetic card or other digital key-like device, along with an operator code or personal identification number (PIN). Regardless of the means employed, if an operator fails to provide suitable information during an included authorization step, usage of the apparatus will most preferably be completely blocked. In addition, a log entry of the failed usage attempt may be recorded in a usage log. Log entries, usage logs, and an associated database(s), will be discussed in significant detail hereinafter.

Once authorized, an operator may next cause an initializing of the photo-thermal epilation apparatus for an epilation session. The initializing may enable the operator to input session related settings. For example, these settings may include indicating how long the session will be and how often each of a succession of high energy light pulses should be generated. When such settings are being provided, suggested settings, which are one of a number of available setting values (determined to be within safe operating limits), are indicated by the operator. The initializing of the apparatus may further include the establishing of a new log entry associated with the upcoming epilation session.

Embodiments of methods of the invention may also provide for a calibrating of the apparatus. Such a calibrating step may be provided after the initializing step, or alternately, as a portion of the initializing step. The calibration activities may be required before each session is conducted, or after a pre-determined number of sessions have been conducted. Additional discussions regarding monitoring and calibrating activities will be discussed hereinafter in detail when referring to FIGS. 6 through 8B.

After the apparatus is initialized/configured, and possibly calibrated, the conducting of the epilation session may commence. During each session a pre-determined succession of high energy light pulses are generated. The apparatus is structured such that each generated light pulse is deliverable to a follicle selected by the operator of the session. A delivering of a respective light pulse causes a photo-thermal epilation of growth support tissue of the selected follicle. After the succession of light pulses of the session have been generated and delivered, a recording of additional portions of the log entry within the usage log may be completed. The recorded information may include a plurality of items associated with the apparatus, the session, the client/patient, and the operator. A plurality of preferred information items forming a log entry may include:

a) date and time stamps of the session;

b) operator related information, including a name and or an identification code of the operator;

c) patient related information, including a name, address, credit card information, and or an identification code of the patient/client;

d) a total number of flashes employed for the session;

e) a total cumulative number of flashes generated since a most recent servicing of the apparatus;

f) a duration of the session;

g) a total duration of all sessions that have occurred since the most recent servicing; and h) dates of recent and or upcoming servicing events.

It may be noted that items such as date and time stamps, a duration of the session, a total number of flashes employed, etc., may be termed session related information.

Methods of the invention may further provide for an automatic monitoring of the operation and usage of the epilation apparatus. For example, the methods may include additional or alternate steps, such as possibly providing usage limit reminders, wherein if it is determined that a pre-determined first usage limit of the apparatus has been reached, for example, indicating that the apparatus requires a periodic servicing, the operator may be so notified (in any suitable fashion). Such a notification may indicate that there are a specific and predetermined number of sessions remaining before use and operation of the apparatus will be blocked, at which point a servicing of the apparatus must be effected. Accordingly, if an attempt to use and operate the apparatus occurs, and it has been determined that a second pre-determined usage limit has been reached, which is greater than the first usage limit by the predetermined number of sessions, any further use of the apparatus will not be permitted until the apparatus receives servicing.

It may be noted that the second limit may be set to be a preferred level or count above the first usage limit, as determined by a number of possible factors. These factors may include both operational considerations and limitations, as well as financial considerations.

In the most preferred embodiments of the invention that support usage limits, and a possible blocking of the use of an apparatus when, for example, a second usage limit has been reached, it may be advantageous to inform an operator of approaching or reached limits immediately upon powering-up the apparatus, or immediately after an authorizing of the operator is successfully completed. That is, it may be preferable to immediately determine if a limit is approaching or has been reached, and inform the operator, before the operator commences possibly meaningless initialization and configuration activities.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIG. 4 provides a schematic diagram of a most preferred embodiment of an energy storage module, including a 'waveshaping' capability, to produce a flattened and extended current pulse that is coupled to energize a flash lamp (when triggered).

FIGS. 5A and 5B illustrate in a simplified form, several embodiments of tapered (needle-less) probes for use with a photo-thermal epilation apparatus of the invention.

Figure 1:
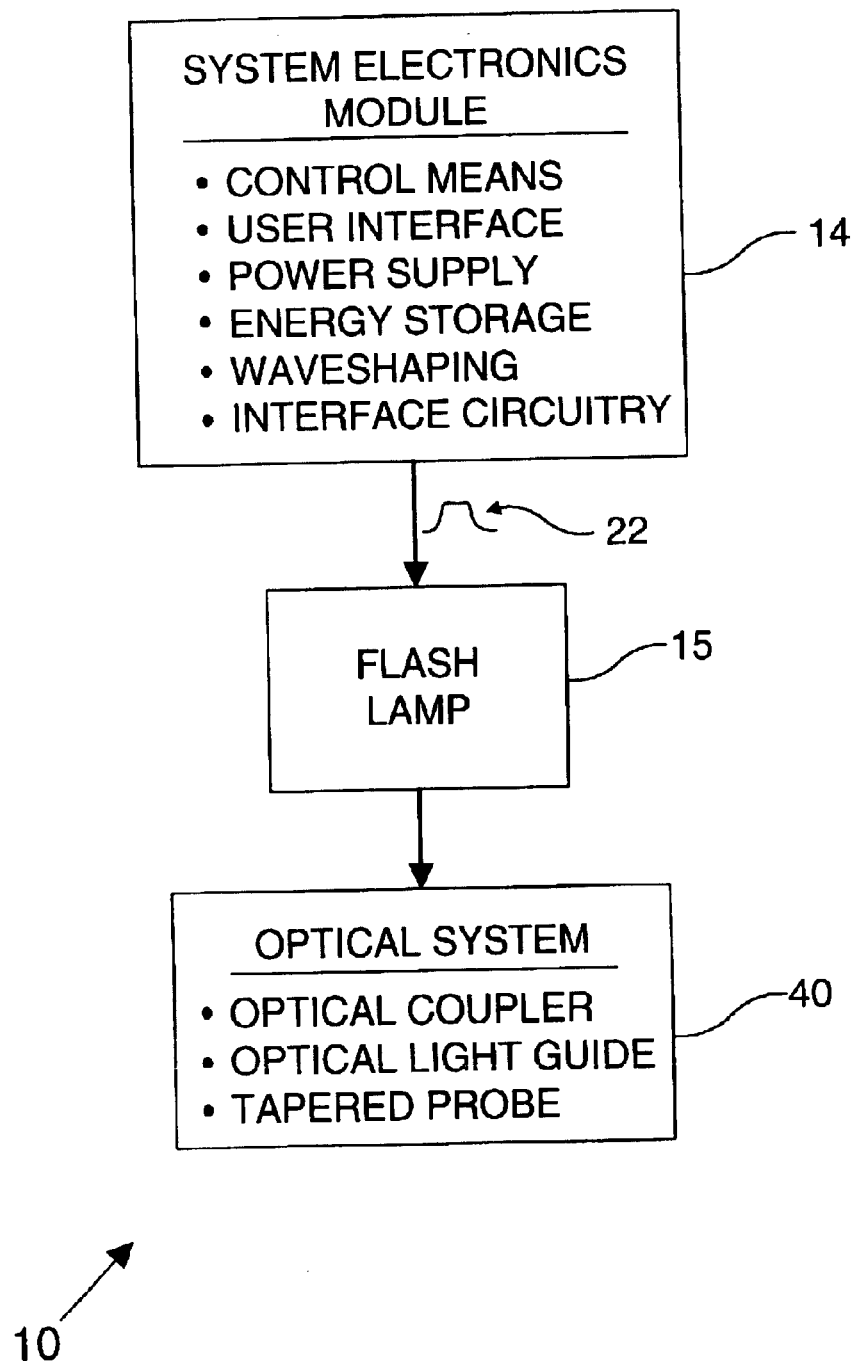
FIG. 1 depicts a high level conceptualized block diagram of a photo-thermal epilation apparatus with which the methods of the invention may be employed.

PARTIAL LIST OF REFERENCE NUMERALS 10, 10a—photo-thermal epilation apparatus
14—(system) electronics module
15—flash lamp
16—flash lamp assembly
16a—energy input coupling (of flash lamp assembly 16)
16b—trigger input terminal (of flash lamp assembly 16)
22—(flattened and extended) current pulse
26—power source
30—power supply module
30a—output of power supply 30
32—energy storage module
32a—output (from the energy storage module 32)
34—charged delay line
36—inductor
38—capacitor
40—optical system
42—optical coupler
46—optical light guide
46a—first end (of optical light guide 46)
46b—second end (of optical light guide 46)
48—detachable optical coupling
60—(tapered needle-less) probe 60
60a—output end (of probe 60)
62—optical light guide portion
64—embedded computer (with user interface)
66—embedded controller module
66a, 66b—operative links
66c—trigger signal
68—tube (of probe 60)
74—computer and user interface
88—detection means
90—calibration portal

DETAILED DESCRIPTION AND MODES OF THE INVENTION

It is important to establish the definition of a number of terms that will be used throughout this disclosure. The terms 'high energy light pulse' and 'light pulse' may be assumed to indicate a light pulse having a sufficient total energy to effect photo-thermal epilation of growth support tissue of a selected hair follicle. The term 'log entry' may be assumed to indicate an information holding data item or series of items that are created in a suitable storage structure that can hold information associated with one or more epilation sessions conducted with apparatus of the invention. Such a log entry may be collected in a searchable 'usage log', which certainly may be provided by any of a number of available databases available to skilled persons. The term 'servicing', as used in the context of this disclosure, may be assumed to include any and all activities performable by authorized and or trained individuals upon a photo-thermal epilation apparatus enabling the epilation apparatus to again be safely and effectively operated for conducting a plurality of epilation sessions (before the next servicing event is required). A number of other terms and definitions will be provided in the discussions that follow, as required, in order to provide for a clear and complete understanding of the present invention.

Many prior art photo-thermal epilation systems include a pulsed power source, which is operatively coupled to a flash assembly. Often an operator activated pedal or button is included for manually activating a flash lamp to produce a high energy light pulse. Each light pulse produced may be applied to a hair follicle causing the photo-thermal epilation of the hair follicle.

Turning now to FIG. 1, there is illustrated therein a high level conceptual block diagram of an embodiment of the photo-thermal epilation apparatus 10 in accordance with the present invention. The methods of the present invention may be employed with the apparatus 10, as well as others available in the art. A first major functional block of this exemplary apparatus is provided by a system electronics module 14. The system electronics module 14 may be arranged to include a control means, and a user interface that is operatively coupled to the control means. Also provided is a power supply. A preferred power supply for the architecture of the apparatus depicted in FIGS. 1 through 3 may be structured having an output with a voltage of 400 to 800 volts, and an average output current of approximately 5 to 50 milli-amperes. The energy provided by the power supply of the apparatus 10 is collected and stored in an energy storage and waveshaping arrangement. The energy storage and waveshaping arrangement is included to enable the delivery of a flattened and extended current pulse to efficiently energize a flash lamp assembly (when a flash lamp 15 thereof is triggered). In preferred embodiments the flattened and extended current pulse 22 may have a maximum instantaneous current level of approximately 1500 to 5000 amperes. The flash lamp 15 produces a high energy light pulse each time it is triggered. A triggering of the flash lamp causes a current pulse 22 to be produced and delivered to the flash lamp and converted to light and heat. Each respective light pulse is most preferably coupled to an optical system 40 and delivered to effect photo-thermal epilation of growth support tissue of a selected hair follicle.

Figure 2:
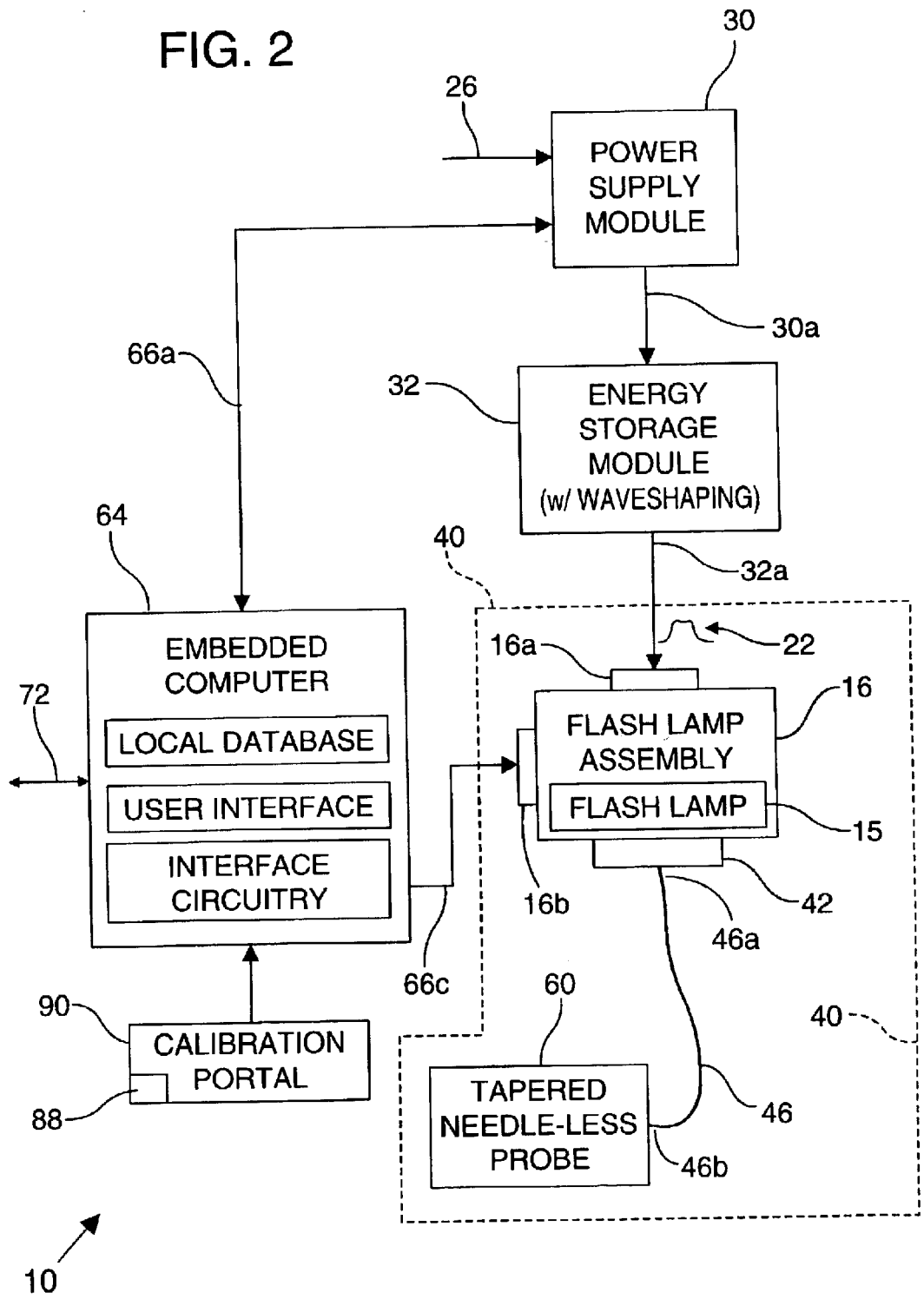
FIG. 2 provides a block diagram of a first preferred embodiment of an epilation apparatus in accordance with the invention.
Figure 3:
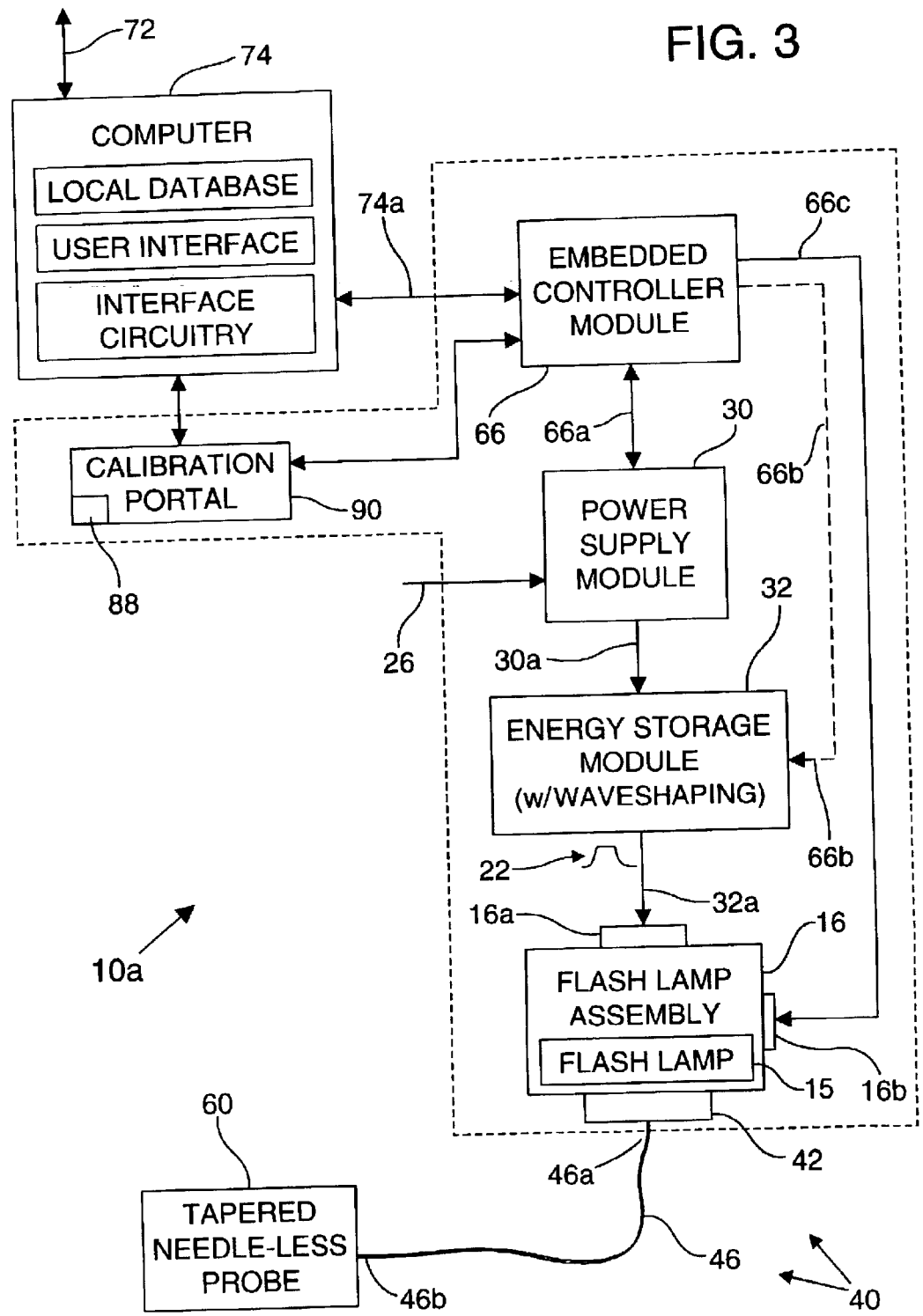
FIG. 3 provides a block diagram of another preferred embodiment of the present invention.

Referring now to FIGS. 2 and 3, there are provided therein block diagrams for two exemplary embodiments of a photo-thermal epilation apparatus 10 that may be operated using methods of the present invention. Before discussing details of the methods of the invention, a concise operating overview of each of these embodiments will be provided for completeness. A power supply module 30 is included that is coupled to a power source 26. Power supply module 30 is configured with an output 30a that provides energy that is collected during an interval between each produced high energy light pulse. It may be noted that the power supply module 30 may continue to supply energy even as the light pulse is produced. However, the amount of energy supplied by the power supply 30 during the short duration of the light pulse is quite small, and is negligible. The output 30a of the power supply 30 is coupled to an energy storage module 32, which is provided for several reasons. First the energy storage module 32 is arranged for collecting and storing sufficient energy. The energy collected and stored is coupled to an energy input coupling 16a of a flash lamp assembly 16, for properly energizing the flash lamp 15 when triggered. Further, the energy storage module 32 has an output 32a configured with a characteristic network impedance, which may be termed Z(network), that is importantly matched to the impedance (Zin) of the flash lamp assembly 16 (during the period that the flash lamp 15 is triggered). That is, when triggered, the input impedance of the energy input coupling 16a of the flash lamp 15 is matched to the output impedance of the energy storage module output 32a when the flash lamp 15 is energized and producing a light pulse. As such, the output 32a of the energy storage module 32 may be said to be 'impedance matched to the flash lamp 15' of the flash lamp assembly 16. This impedance matching arrangement supports the efficient delivery of a flattened and extended current pulse 22 to energize the flash lamp 15. For example, a most preferred embodiment of an energy storage module 32 of the invention is depicted in FIG. 4. This completely passive embodiment is structured with a plurality of capacitors 38 and a plurality of inductors 36, as shown, arranged in what will be termed a 'series-parallel configuration'. The series-parallel arrangement of FIG. 4 may also be referred to as a charged delay line 34. It may be noted that the values of each inductor, and each capacitor, respectively, may not be identical.

Returning the FIGS. 2 and 3, in order to enable the high energy light pulse to be suitably delivered to a selected follicle, the light pulse produced by the flash lamp assembly 16 (or more accurately the flash lamp 15) is delivered to the follicle by the optical system 40. The optical system 40 may be assumed to include the flash lamp assembly 16, an optical coupler 42, and a means to efficiently deliver the energy of the light pulse to the follicle. The optical coupler 42 is therefore structured to 'efficiently' (i.e., with minimum losses) couple the light pulse into a first (input) end 46a of an optical light guide 46. The optical light guide 46 is structured to cause the delivery of the light pulse, with minimal losses, to a second end 46b of the light guide 46. It should be understood that the term 'efficiently' may be assumed to be a relative term indicating that a reasonable amount of the light energy associated with the light pulse produced by the flash lamp assembly, say in the range of 10% to 60% of the total energy produced, is coupled into the optical light guide 46 at the first end 46a. The optical light guide 46 may be provided by any suitable standard optical fiber or liquid core optical fiber. In a most preferred embodiment, light guide 46 is provided with a nominal diameter of 3 to 6 millimeters. As can be seen in FIGS. 2, 3, 5A, and 5B, a tapered needle-less probe 60 is provided at the second end 46b of the optical light guide 46. The probe 60, which may be structured with a holding tube 68 (see FIGS. 5A and 5B), is arranged to receive the light pulse coupled into the first end 46a of the light guide 46 to effect the desired delivery of the light pulse to the second end 46b. As the light pulse passes through an optical light guide portion 62, including a narrowed end portion at an output end 60a of the probe 60, the light density is increased. As such, this higher density light energy is emitted from the probe tip 60a, and immediately epidermically received and delivered to a selected hair follicle by way of the tapered needle-less probe 60. As shown in FIGS. 5A and 5B, the probe may be fixed to the second end 46b (FIG. 5A) or removably attached via a detachable optical coupling 48 (FIG. 5B).

Returning again to FIGS. 2 and 3, the apparatus thereof may further include control and or computing means to support their operation. For example, the embodiment of FIG. 2 is depicted with an embedded computer 64 (having a user interface), which may be very generally termed a 'control means' or a 'control and data logging means'. The embedded computer 64 is provided to control the operation of the photo-thermal epilation apparatus 10, and further to support or enable a number of functional and or operational features and characteristics of the methods of the present invention. For example, as can be seen in FIG. 2, the embedded computer 64 is arranged to periodically trigger the flash lamp assembly 16 via an operative link 66c that is coupled to the trigger terminal 16b. Also, an operative link 66a may be employed to vary, say, the output voltage level of the power supply module 30 during calibration activities.

Continuing with FIG. 2, it is contemplated that the trigger terminal 16b would be employed to trigger the flash lamp 15 of the flash lamp assembly 16 at a pre-determined rate or cadence (say once every second) for a pre-determined length of time (say 15 to 60 minutes). Such a length of time may also be termed a 'temporal interval', and define a 'session'. Accordingly, during a session a series of light pulses may be produced in spaced temporal succession. A portion of the energy produced by each light pulse is coupled into the optical light guide 46 at a first end 46a. The light pulse energy then travels along the optical light guide 46 to a second end 46b, where it is concentrated and delivered to a selected hair follicle, via the probe 60, causing the desired photo-coagulation of the growth support tissue thereat. Greater details of preferred operating methods of the invention will be provided and fully discussed when referring to FIGS. 6 through 9B.

The embedded computer 64 may be provided by skilled persons having a number of varying structures and configurations. For example, microcontroller or microprocessor based designs are possible. Alternatively, commercially available single board computers may be employed. In addition, the user interface (not illustrated) may be structured to include a keypad, momentary and maintained switches, and a suitable multi-character display unit. It is important to understand that any design approach, even possibly those based on custom ASIC and SOC solutions, which provide or support the required functionality are contemplated as being within the scope of the 'control means' of the present invention. Further, any user interface structure that enables an exchange of required information between an operator and the system, possibly including voice activated user interface components, should also be considered within the scope of the invention.

Another important operational feature provided by embodiments of the invention, which may certainly be included with the embodiments of FIGS. 2 and 3, enables (or requires) an operator to calibrate the amount of energy delivered to an output end 60a (see FIGS. 5A and 5B) of the probe 60 with each light pulse produced by the flash lamp 15 and delivered thereto. Such a calibration activity may be required before use of the apparatus is permitted. Therefore, an operator may be required to calibrate the apparatus before or after each session, after a predetermined number of sessions, after a predetermined number of light pulses have been delivered, etc.

To support an accurate and rapid calibration of the apparatus of the invention at the location of use, a calibration portal 90 may be included and structured to accept the output end 60a of the probe 60. The calibration portal is configured to receive a precise sample (or known portion) of the light pulse energy delivered to said output end 60a when inserted into calibration portal. The term 'precise sample' is to be defined as a known portion of the light pulse energy, which is employed to enable calibration of the light pulse intensity to a desired pre-determined intensity level. As such, this feature will enable an operator to periodically calibrate the photo-thermal epilation apparatus 10 or 10a to compensate for a number of phenomenon including the aging of the flash lamp 15, the 'drifting' of system electronic components or modules, etc. The calibration portal 90 may be embodied to include one or more known off-the-shelf photo-sensitive devices. One preferred device that may be utilized is a PIN diode (not shown), which would typically be structured with an optical window. Other photo-sensitive devices, as well as required signal conditioning circuitry needed to embody the calibration portal 90, may certainly be provided by skilled persons.

In a most preferred embodiment, the calibration portal 90 would be structured with a detection means 88 that would enable the apparatus 10/10a to determine when the output end 60a of the probe 60 is properly inserted into the calibration portal. Once the probe 60 is properly inserted into the calibration portal 90, an on-board control means, such as embedded computer 64 or embedded controller module 66, may cause the flash lamp 15 to be triggered one or more times so that the energy level of the light pulses received by the calibration portal 90 may be adjusted to desired levels.

Another possible structure that may be provided with apparatus of the invention is illustrated in FIG. 3. It may be noted that for the embodiment shown, the operation of the power supply module 30, flash lamp assembly 16 (including flash lamp 15), optical coupler 42, optical light guide 46, and a probe 60 are as discussed above. However, the embodiment of FIG. 3 is structured with an embedded controller 66 and an external computer 74 (providing at least a portion of a user interface). For example, the computer 74 may most preferably be provided by a notebook-style portable computer, or a desktop type of personal computer. Accordingly, the computer 74 is contemplated to include a keyboard and display (not explicitly shown), which enables an operator to input and verify operational and other system/client information. This information may include items such as billing and or credit data, calibration and or maintenance information, client related data, operator guidance, assistance, or training information, available session credits, session debits accumulated, etc. Clearly, such a user interface would enable an operator to establish the pre-determined rate to periodically trigger the flash lamp 15 and or select the length of the time for an impending epilation session. Accordingly, a portion of the information provided to the computer 74, may be supplied to or provided (as necessary) to the embedded controller module 66 by way of operative link 74a. In a preferred embodiment, operative link 74a would be provided by a suitable hardwired, optical, or wireless communication channel. In a most preferred embodiment link 74a may be realized by common interfaces such as a universal serial bus (USB) or a common RS-232C serial channel.

As illustrated in FIGS. 2 and 3, a communication channel 72 may further be included to enable the photo-thermal epilation apparatus 10 or 10a to be linked via a communication network to a remote system (not explicitly illustrated). The linking to the remote system may be employed for a variety of reasons including billing purposes, remote monitoring considerations, updating of system operating software, user training and evaluation, insuring calibrated and safe operation, recording usage, enabling a count of pre-paid sessions to be loaded into a local computing device (such as embedded computer 64), blocking unauthorized usage, etc. An interface to communication channel 72 may be provided by a modem, network interface card, a wireless link, an optical link, or other known communication supporting arrangements that may be available.

Turning now to FIGS. 6 through 8B, a number of embodiments of the invention will now be discussed. A first preferred and basic method of operation is provided by the high level flow chart of FIG. 6. This method may commence at 100 with an identifying of the operator. For example, each authorized operator may be required to provide the equivalent of a personal identifier, a user number, and or a login name, preferably followed by a password or personal identification number (PIN). At 104 a check is made to verify the operator is authorized to use the apparatus. For example, the use and operation of the apparatus may be blocked for any of the following reasons:

a) operator is not known (for example not listed in a list of authorized operators);

b) the password or PIN is incorrect; and c) the operator is not authorized to operate the apparatus based upon an established criteria, such as the current time and or date, a serial number of the apparatus, etc.

If not authorized, the method may record the unauthorized attempt at 112 and subsequently terminate at 114. However, if at 104 it is determined that the operator is authorized, at 106 the apparatus may be initialized and configured for a photo-epilation session. The initializing of the apparatus may include a number of possible steps and activities. For example, one or more of the following may occur during an initializing and configuring of an epilation apparatus of the invention:

a) an inputting of session related items possibly indicating how long the session will be and a cadence for the succession of high energy light pulses to be generated;

b) establishing a new log entry associated with the upcoming epilation session within a suitable usage log or database;

c) conducting calibration activities wherein the energy level of one or more 'test' light pulses is verified to be at a specified level or within a pre-defined range;

d) recording of date and time stamps of the session;

e) recording of the identity (e.g., storing an associated ID code) of the operator;

f) entering the name, address, etc., of a new client; and g) numerous other possible items and actions that may be included in desired initialization and configuration activities.

At 108, the session is conducted with a succession of high energy light pulses generated in a temporally spaced fashion for the duration of the session, or until the operator halts or pauses the generating of the light pulses. At a convenient time, preferably immediately after a session is completed, an entry in a usage log is either completed, if already created during initialization, or created and completed at 112. The completing of the log entry may include a recording of any items listed above that have not been (or could not be) recorded during the initialization step. In addition, operational information such as total sessions conducted and total flashes generated may be updated.

Figure 6:
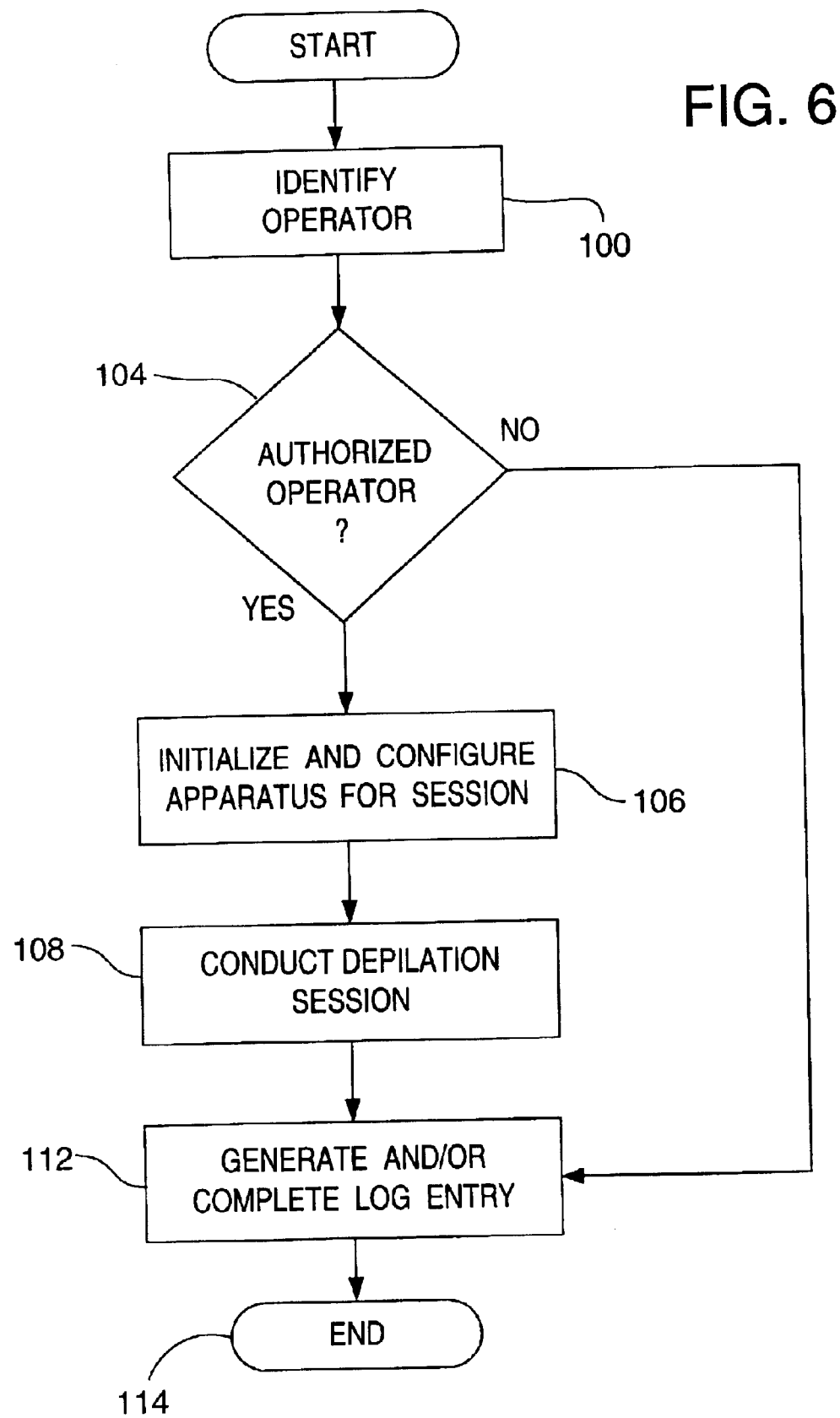
FIG. 6 depicts a simplified flow chart of a first preferred embodiment of a method of operating a photo-thermal epilation apparatus in accordance with the invention, wherein the embodiment includes steps providing for a maintaining and updating of a basic usage log for the apparatus.
Figure 7:
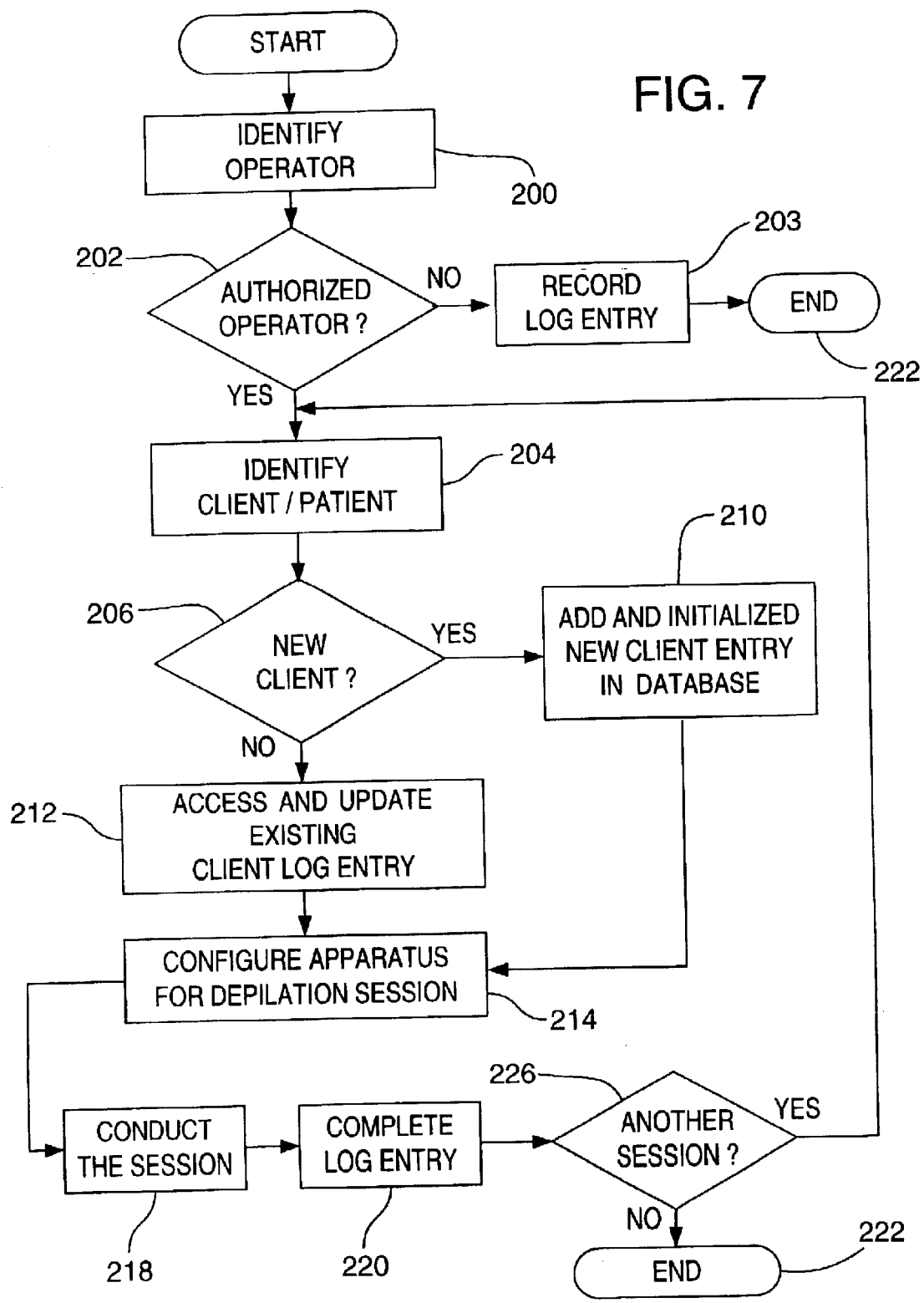
FIG. 7 depicts a simplified flow chart of another preferred embodiment of a method of operating an epilation apparatus of the invention, wherein the usage of the apparatus is monitored and recorded by way of entries collected and organized within a database.

The method of FIG. 6 may be considered a basic operating method as it may not include additional, possibly advanced features and activities of the method of the present invention. For example, as will be fully discussed when referring to FIGS. 7 through 9B, a variety of limits, allotments, etc., may be provided to control access to, and usage of epilation apparatus in accordance with the invention. Referring now to FIG. 7, another preferred embodiment for operating an epilation apparatus of the invention is depicted by flow chart, again in a possibly somewhat simplified form. Importantly, this method most preferably utilizes a database, or an equivalent data holding structure and logic to access and store data including usage log entries. As with the method of FIG. 6, the method may commence at 200 with an identifying of the operator, and is followed by an authorization check at 202. If the user is not authorized, at 203 a log entry may be made, and the method terminates at 222. However, if authorized the method of FIG. 7 may provide for an indicating or selecting of a client name at 204. For example, a list of clients and patients may be provided to the operator. Alternately, the operator may enter the last name of the client, possibly being provided with a list of all clients having that last name presently entered in the database. If the client name is not known, the operator may enter additional information associated with the new client, possibly causing an entry or record in a database to be established in the process. Accordingly, at 206 a check is made to determine if the client name exists in the database. If a new client, at 210 the entry may be created. If not a new client, access is provided at 212 to update or append an existing client/patient database or log entry items. After an entry is updated, appended to, or created, as required, the apparatus may be configured at 214 for an epilation session. At 218 the session is conducted, and at 220 the database and or log entry is completed, as required. At 226, a check may be provided to determine if the same operator is going to conduct another session. If so, the method may repeat at 204, as illustrated, or possibly most preferably at 200 (wherein the operator must again be identified and authorized). If at 226 it is determined that no further sessions are to be conducted by the present operator, the method may terminate at 222 by suitably closing the usage log and 'logging-out' the operator. Further use of the apparatus is preferably blocked until another authorized operator is identified.

The most preferred embodiments of the invention provide for a blocking of the use of an epilation apparatus for any one of a number of possible reasons or causes. For example, possible reasons may include:

a) unauthorized operator;

b) usage limit reached (service required);

c) over-due balance on an account associated with operation of a rented, leased, or consigned epilation apparatus; and d) depletion of all available pre-paid epilation sessions.

Figure 8A:
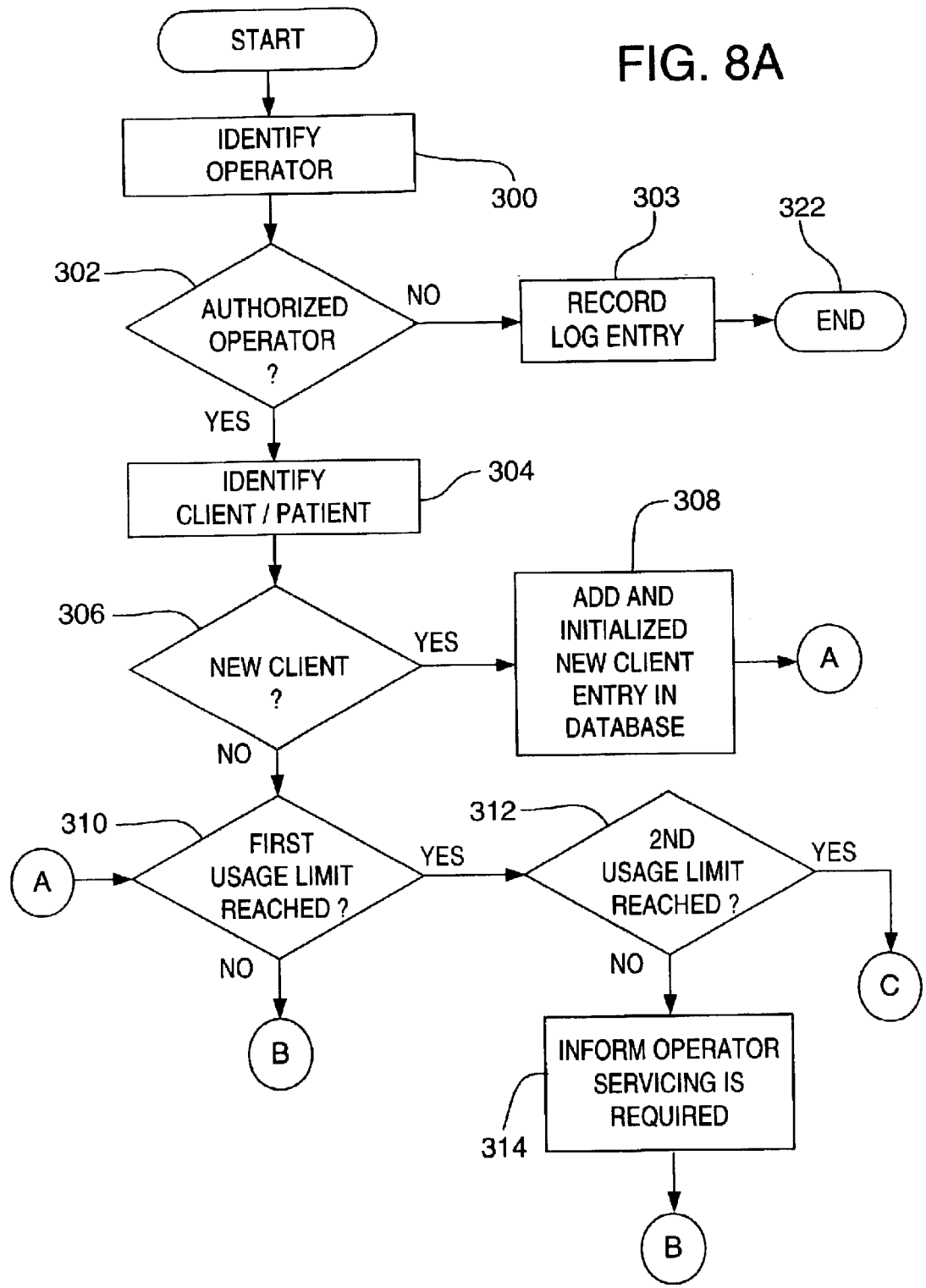
FIGS. 8A and 8B provide a flow chart of another more advanced embodiment of a method of operating a photo-thermal epilation apparatus of the invention with this embodiment including steps for determining when usage of the apparatus must be blocked due to one or more usage limits being reached.
Figure 8B:
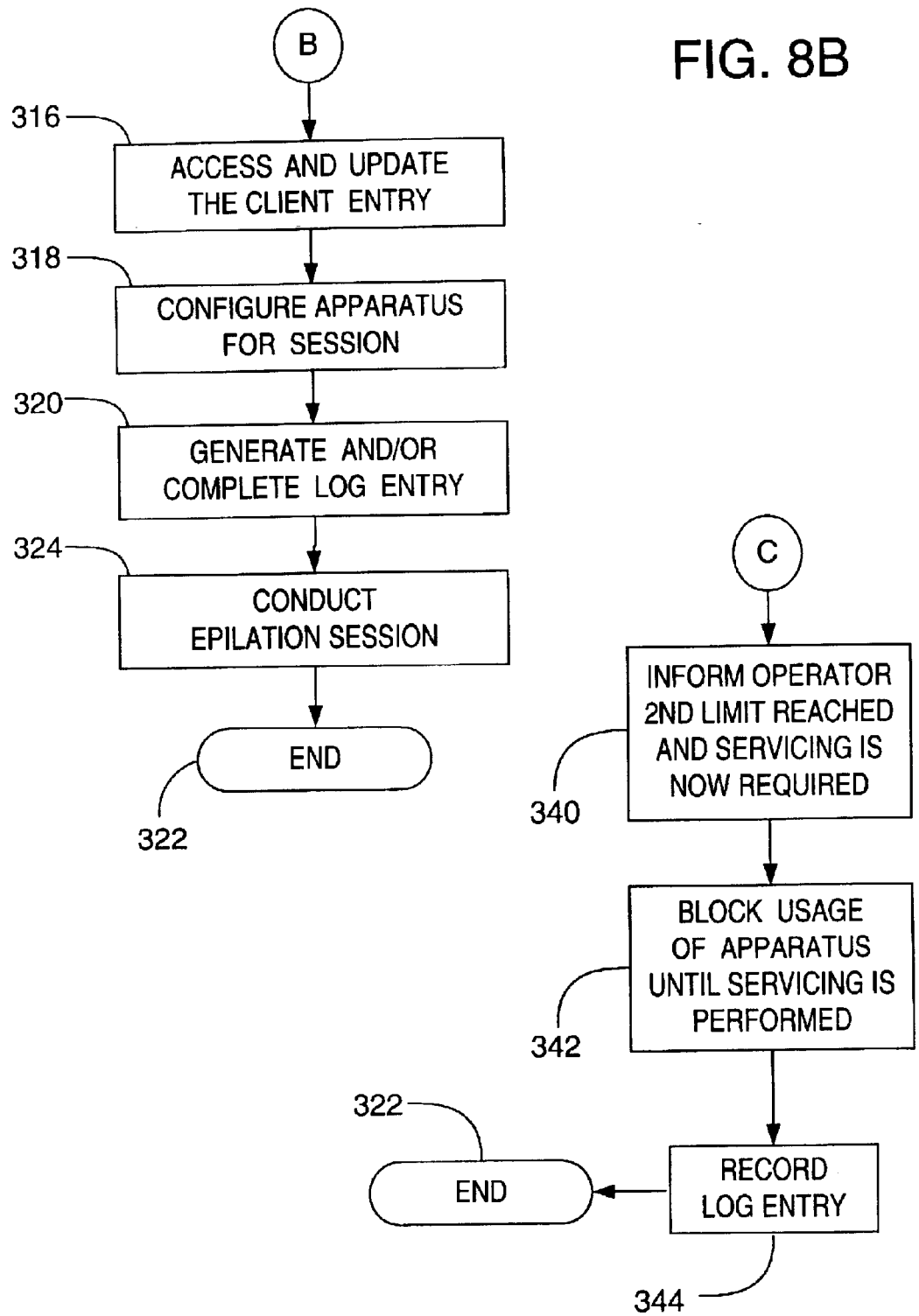

Turning to FIGS. 8A and 8B, there is provided a flow chart of an embodiment of the method of the invention wherein a usage limit is checked to determine if operation of the unit should be enabled. The method may begin in like fashion to the methods of FIG. 6 and FIG. 7, wherein the operator is identified at 300. Should the operator be determined at 302 not to be an authorized user, at 303 a log entry may be recorded, and usage of the apparatus blocked at 322. If authorized, the method may require the operator to identify the client of the session at 304. If the client is determined to be a new client at 306, then client related information may be input and stored in a log entry or a suitable database, as required, at 308. Next, at 310 the method calls for a check to determine if a pre-defined first usage limit has been reached. The actual usage limit may be established, for example, during the manufacture of the apparatus, during a recent servicing, or as a result of a periodic exchange of information with a remote computer. If the first usage limit has not been reached, control is transferred via connector-B to FIG. 8B (as will be discussed below).

If at 310 it is determined that the first usage limit has been reached, at 312 another check is performed to determine if a second usage limit has been reached. If at 312, the second usage limit has not been reached, the operator is informed that the first limit has been reached (or exceeded) and that a user action is required. For example, an authorized servicing may be required. Additionally, a message may be provided informing the operator as to how many epilation sessions are still available before usage of the apparatus is blocked. Via connector-B, once the operator has been informed that the first usage limit has been reached, at 316 the operator may access and update a client entry, as required or desired. Next, at 318 the epilation apparatus is configured (as discussed above). At 320, an epilation session is conducted.

Once an epilation session has been conducted, the method provides for the generating and or completing of a log entry at 324 that is associated with the just completed session. The method may then terminate at 322 (as illustrated) or continue by determining if the operator needs to conduct additional sessions (as previously discussed when referring to the method of FIG. 7).

If at 312 it is determined that the second usage limit has been reached, connector-C transfers control to FIG. 8B, where at 340 the operator is informed that the second usage limit has been reached and at 342 usage of the apparatus is blocked. The apparatus must now be serviced before further use of the apparatus is permitted. The embodiment of the method of the invention of FIGS. 8A and 8B, may also cause the epilation apparatus to attempt to establish a connection to a remote computer (not explicitly illustrated). If such a connection is established, the connection may be employed to indicate to a remote entity that the apparatus requires service. The remote entity may respond by contacting one or more individuals at the location of the apparatus in order to arrange for the apparatus to be sent in for service, or to arrange an appointment for on-site servicing.

Figure 9A:
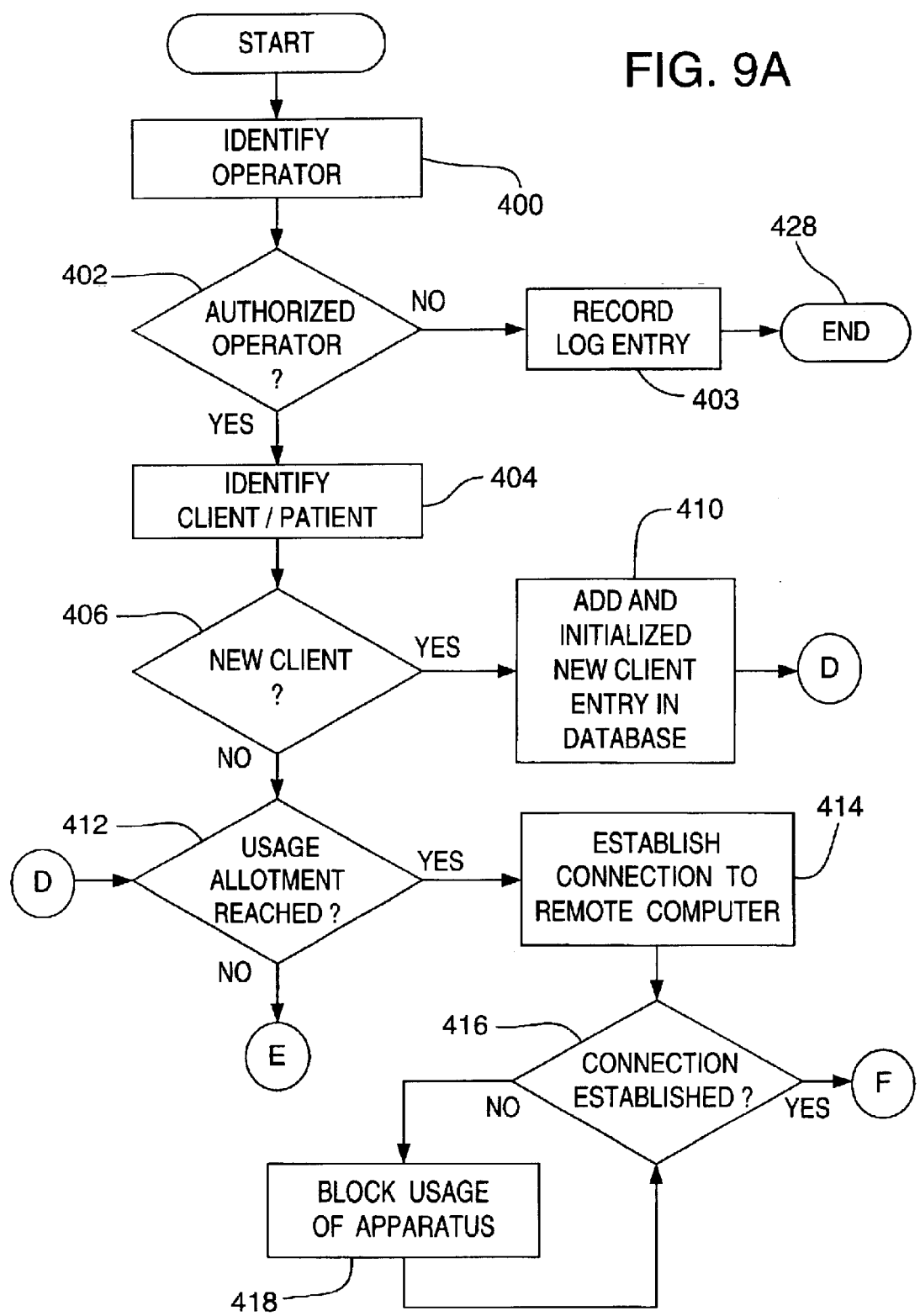
FIGS. 9A and 9B provide a flow chart of yet another advanced embodiment of a method of operating a epilation apparatus of the invention, including steps for determining when a usage allotment has been reached, resulting in a blocking of the usage of the apparatus.
Figure 9B:
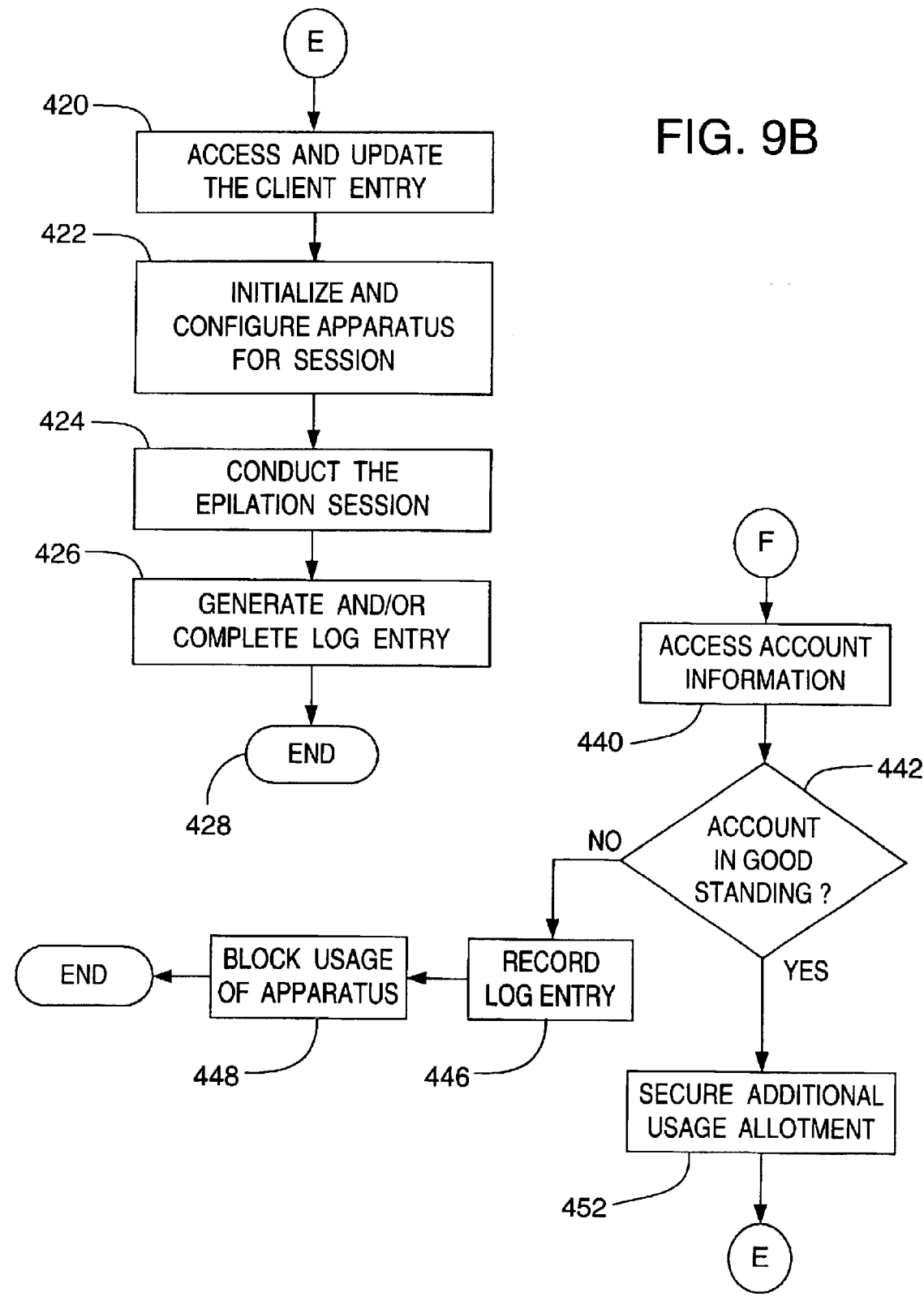

Referring now to FIGS. 9A and 9B another preferred embodiment of the invention will be discussed. This embodiment provides for the blocking of usage of the apparatus when a 'usage allotment' has been reached. The usage allotment may be associated with a reaching of a maximum balance-due level or the depletion of all available pre-paid epilation session credits. A blocking of the apparatus due to the former situation is do to the reaching of a credit limit. While the latter situation results in blocking of the usage due to the using up of all available pre-paid session credits. Other criteria related to payments for use of epilation apparatus are possible and are certainly within the scope of the invention.

As can be seen in FIG. 9A, the method may begin in like fashion to the methods of FIG. 6 and FIG. 7, wherein operator is identified at 400. If determined not to be an authorized user at 402, a log entry may be recorded at 403, with usage of the apparatus blocked at 428. If authorized, the method may require the operator to identify the client at 404. If the client is a new client, at 410 client information is input and stored in a log entry or a suitable database for future use. Next, at 412 the method calls for a check to determine if an available usage allocation has been reached. If the usage allocation has been not been reached, control is transferred via connector-E to FIG. 9B (as will be discussed below).

If at 412 it is determined that a usage limit has been reached, this embodiment of the invention, may cause the apparatus to attempt to establish a connection to a remote computer at 414. It may be noted that the establishing of the link may actually occur as a result of a prompt being provided to the operator. In this latter case, the operator may be instructed to cause the connection to be established. If it is determined at 416 that the connection is not established (say within a pre-defined temporal interval), usage of the apparatus is blocked at 418 until the connection is established, followed by the transferring of control via connector-F to 440 of FIG. 9B.

Once the connection is established at 440, available account information may be accessed. This account information may be accessed by way of an exchange of information between an epilation apparatus employing the method of the invention and a remote computer. As shown in FIG. 9B, if the account associated with the apparatus is found to be in good standing at 442 (e.g., no outstanding or overdue balances or sufficient credit available), an additional usage allotment for future sessions may be secured at 452. The securing of the allotment of sessions, may result for example, in an automatic billing of a known cost for the sessions, or result in a suitable debiting of a selected or indicated account, or other actions providable by skilled persons. Once an additional usage allotment has been secured at 452, control is transferred via connector-E to 420 of FIG. 9B. If the account is determined not to be in good standing at 442, a log entry may be made at 446, with usage blocked at 448.

When control is transferred to connector-E, at 420, the operator may access and update a client entry, as required or desired. Next, at 422 the epilation apparatus may be initialized and configured (possibly including some or all of the activities discussed above). At 424, an epilation session is conducted. At 426, a log entry may be created, recorded, and or completed. The method may terminate at 428 (as illustrated) or continue by determining if the operator needs to conduct additional sessions (as previously discussed when referring to the method of FIG. 7).

While there have been described herein a plurality of the currently preferred embodiments of the method of present invention, those skilled in the art will recognize that other and further modifications may be made without departing from the invention. For example, when considering the embodiments of FIGS. 8A through 9B, it may be most preferable to determine if usage, allotment, or other possible limits have been reached earlier in the methods than has been described. Accordingly, a possibly most preferred method may determine if an operator is authorized, and then determine if one or more limits have been reached before identifying the client and or entering client related information. In addition, another most preferred embodiment of the invention may call for a combination of usage, allotment, and or other available limits to be checked before usage of a respective epilation apparatus of the invention is permitted for conducting one or more epilation sessions.

Accordingly, the foregoing descriptions of the specific embodiments of the present invention have been presented for the purposes of illustration, description, and enablement. They are not intended to be exhaustive or to limit the invention to the specific forms disclosed and or illustrated. Obviously numerous modifications and alterations are possible in light of the above teachings, and it is fully intended to claim all modifications and variations that fall within the scope of the appended claims provided hereinafter.

What is claimed is:

1. A method of operating and monitoring usage of a photo-thermal epilation apparatus comprising the steps of:
   a) identifying and authorizing an operator to conduct a session;
   b) doing one of:
      i) blocking usage of the apparatus, if the operator is not authorized, and;
      ii) initializing the photo-thermal epilation apparatus for the session, including establishing of a log entry for the session and determining if a pre-determined first usage limit has been reached, thereby indicating the apparatus requires servicing, and proceeding to step-c;
   c) conducting a session wherein a pre-determined succession of high energy light pulses are generated, with each generated light pulse deliverable to a follicle selected by the operator to effect photo-thermal epilation of growth support tissue of the selected follicle; and
   d) recording in the usage log a log entry comprising information including at least one of:
      i) operator identifying information;
      ii) patient related information; and
      iii) session related information.

2. The method as recited in claim 1, wherein the steps of conducting a session and recording a usage log are supported by a control means, with the control means enabling at least one of:
   a) triggering the flash lamp at a pre-determined rate for a pre-determined temporal duration to produce a series of temporally spaced high energy light pulses during a session;
   b) enabling a recording of each log entry associated with each session;
   c) providing controlled access for inspecting and reviewing log entries; and
   d) establishing a connection to a pre-selected remote system.

3. The method as recited in claim 1, wherein if during the initializing step it is determined that the first usage limit has been reached, the operator is notified that the apparatus requires servicing.

4. The method as recited in claim 3, wherein if during the initializing step it is determined that a second pre-determined usage limit, which is greater than the first usage limit, has been reached, further use of the apparatus is not permitted until the apparatus receives servicing.

5. The method as recited in claim 1, wherein the step of recording an entry in the usage log includes recording at least one of:
   a) a date of the session;
   b) a starting time stamp;
   c) an ending time stamp;
   d) an identification code of an operator conducting a session;
   e) a name of the operator;
   f) a total number of flashes employed for a session;
   g) a total cumulative number of flashes generated since a most recent servicing of the apparatus;
   h) a duration of the session;
   i) a total duration of all sessions that have occurred since the most recent servicing;
   j) a date of the most recent servicing; and
   k) an estimated date of a next servicing.

6. The method as recited in claim 1, wherein the step of conducting a session and delivering high energy light pulses to respective follicles is enabled by including an optical probe, which is structured with a tapered needle-less tip, that is manipulated by the operator.

7. The method as recited in claim 6, wherein an additional calibrating step is included before conducting the session, wherein the additional step includes an inserting of the tip of the needle-less probe into a calibration portal of the apparatus that is structured to accept the tip such that a precise sample of a light pulse emitted from the tip is measured and employed for adjusting and calibrating light pulse intensity to a predetermined desired level.

8. The method as recited in claim 7, wherein during the calibrating step, if it is determined that the light pulse intensity produced can not be adjusted to the predetermined desired level, the operator is so notified, and further use of the apparatus is not permitted until the apparatus receives servicing.

9. A method of conducting an epilation session, and monitoring and logging the use of a photo-thermal epilation apparatus structured with a tapered needle-less probe having a tip from which a high energy light pulse is deliverable to an operator selected hair follicle to cause photo-thermal epilation of growth support tissue of the selected follicle, the method comprising the steps of:

a) identifying and authorizing an operator, and if the operator is not authorized for using the apparatus, doing at least one of:
        i) blocking usage of the apparatus; and
        ii) creating and recording a log entry indicating an unauthorized usage attempt;
    b) initializing the photo-thermal epilation apparatus, wherein if it is determined that any one of:
        i) a pre-selected number of log entries have been recorded;
        ii) a pre-selected usage limit has been reached;
        iii) an allotment limit has been reached;
at least one of the following action to occur:
        iv) the operator is notified that the limit has been reached and a limited number of additional sessions will be permitted;
        v) the operator is notified that the limit has been reached and usage of the apparatus is blocked; and
        vi) an attempt is made to connect to a remote computer to enable a transmitting and exchanging of information with the remote computer;
    c) establishing a log entry associated with the session, the log entry including one or more of:
        i) a date of the session;
        ii) a time stamp indicating a start time of the session;
        iii) an identification code of an operator conducting a session;
        iv) a name of the operator;
        v) a total number of flashes employed for a session;
        vi) a total cumulative number of flashes generated since a most recent servicing of the apparatus;
        vii a duration of the session;
        viii) a total duration of all sessions that have occurred since the most recent servicing;
        ix) a date of the most recent servicing; and
        x) an estimated date of a next servicing;
    d) starting a usage session;
    e) generating a temporally spaced succession of high energy light pulses for the duration of the session, each light pulse deliverable to a selected follicle to cause photo-thermal epilation of growth support tissue thereat;
    f) ending the session wherein light pulse generation is terminated; and
    g) completing the log entry comprising information associated with the session just conducted, including a second time stamp indicating a stop time.

10. The method as recited in claim 9, wherein during the initializing step, and after it is determined that one of the limits has been reached, should an attempt at connecting with the remote computer fail, operation of the apparatus is not permitted until a connection to the remote computer is established and utilized for transmitting and exchanging the information.

11. A method of operating and monitoring the usage of a photo-thermal epilation apparatus structured for delivering high energy light pulses to each of a succession of selected follicles for causing a photo-thermal epilation of growth support tissue of each of the follicles, the method comprising the steps of:

a) identifying and authorizing an operator, and if authorized, permitting an initializing and configuring of the apparatus for an epilation session;
    b) establishing of a log entry in a usage log that is associated with the epilation session;
    c) determining if either a pre-selected number of log entries have been recorded or a pre-selected operating limit of the apparatus has been reached, causing an establishing of a connection to a remote computer for transmitting and exchanging information with the remote computer;
    d) doing one of:
        i) blocking usage of the apparatus if connecting to the remote computer fails;
        ii) blocking usage of the apparatus if after connecting to the remote computer attempts to secure an additional allotment of sessions are not successful; and
        iii) permitting the operator to commence the session causing a generating of a pre-determined succession of high energy light pulses, with each light pulse deliverable to a selected follicle by the operator to effect photo-thermal epilation of growth support tissue of the follicle;
    e) determining when one of a predefined number of light pulses have been generated, or a temporal duration of the session has elapsed, thereby indicating an end of the session; and
    f) completing a recording of at least one log entry for the session.

12. The method as recited in claim 11, wherein the step of completing and recording log entries includes storing information in a database.

13. The method as recited in claim 11, wherein an additional step is provided wherein an authorized individual is given access to the database in order to enable at least one of:

a) inspecting and reviewing log entries recorded within the database;
    b) deleting of unneeded log entries; and
    c) archiving log entries.

14. The method as recited in claim 11, wherein if during step-c a connection can not be established with the remote computer, operation of the apparatus is not permitted until a connection to the remote computer is established and a transmitting and exchanging of information establishes that an additional allotment of epilation sessions is available and secured.

\* \* \* \* \*